(12) United States Patent
Papen

(10) Patent No.: US 6,537,817 B1
(45) Date of Patent: Mar. 25, 2003

(54) PIEZOELECTRIC-DROP-ON-DEMAND TECHNOLOGY

(75) Inventor: Roeland F. Papen, Guilford, CT (US)

(73) Assignee: Packard Instrument Company, Downers Grove, IL (US)

( * ) Notice: Subject to any disclaimer, the term of this patent is extended or adjusted under 35 U.S.C. 154(b) by 95 days.

(21) Appl. No.: 09/687,627

(22) Filed: Oct. 13, 2000

Related U.S. Application Data

(63) Continuation-in-part of application No. 09/489,261, filed on Jan. 21, 2000, which is a continuation-in-part of application No. 09/056,233, filed on Apr. 7, 1998, now Pat. No. 6,203,759, which is a continuation-in-part of application No. 08/656,455, filed on May 31, 1993, now abandoned.

(60) Provisional application No. 60/159,701, filed on Oct. 15, 1999, provisional application No. 60/067,665, filed on Dec. 5, 1997, and provisional application No. 60/041,861, filed on Apr. 8, 1997.

(51) Int. Cl.⁷ .............................................. F23D 14/50
(52) U.S. Cl. ................. 436/49; 134/7; 134/8; 134/22.11; 239/106; 239/116
(58) Field of Search ................. 436/49, 54; 134/7, 134/8, 22.11; 239/106, 114, 115, 116

(56) References Cited

U.S. PATENT DOCUMENTS

| | | |
|---|---|---|
| 3,427,480 A | 2/1969 | Robinson |
| 3,452,360 A | 6/1969 | Williamson |
| 3,507,269 A | 4/1970 | Berry |
| 3,512,173 A | 5/1970 | Darmouth |
| 3,549,328 A | 12/1970 | Kilburn |
| 3,666,421 A | 5/1972 | Price |
| 3,683,212 A | 8/1972 | Zoltan |
| 3,711,252 A | 1/1973 | Roy |
| 3,798,961 A | 3/1974 | Flambard et al. |
| 3,831,845 A | 8/1974 | Packt |
| 3,832,579 A | 8/1974 | Arndt |
| 3,838,012 A | 9/1974 | Higgens |
| 3,859,169 A | 1/1975 | O'Driscoll et al. |
| 3,902,083 A | 8/1975 | Zoltan |
| 3,941,700 A | 3/1976 | Sundt .................. 210/223 |
| 3,946,398 A | 3/1976 | Kyser et al. |
| 3,958,249 A | 5/1976 | DeMaine et al. |
| 3,964,871 A | 6/1976 | Hochstrasser |
| 3,975,162 A | 8/1976 | Renn |
| 3,985,467 A | 10/1976 | Kefferson |

(List continued on next page.)

FOREIGN PATENT DOCUMENTS

| | | |
|---|---|---|
| DE | 3 007 189 | 11/1980 |
| DE | 3 014 256 | 12/1980 |
| DE | 3 332 491 | 3/1985 |
| DE | 3 833 586 | 7/1989 |
| DE | 3 915 920 | 11/1990 |

(List continued on next page.)

OTHER PUBLICATIONS

Derwent ACC No. 2000–097138. Eickhoff et al, WO 99/61881, "Micro–dispener for processing substances in smallest sample volumes.", Dec. 12, 1999.*
Ashley et al. "Development and Characterization of Ink for an Electrostatic Ink Jet Printer" pp. 69–74, IBM J. Res. Develop.

(List continued on next page.)

*Primary Examiner*—Jan Ludlow
(74) *Attorney, Agent, or Firm*—Jenkens & Gilchrist

(57) ABSTRACT

A method and apparatus for cleaning the interior of capillary tubes used to dispense 1 to 100 micron diameter liquid droplets by a piezoelectric transducer surrounding each capillary tube. Magnetic particles are aspirated into the capillary tubes and moved by an exterior magnet to cause deposits on the interior walls to be dislodged and subsequently discharged from the capillary tube. In a preferred embodiment, the magnetic particles are coated with a material capable of binding such deposits, e.g., DNA, RNA, and the like.

9 Claims, 5 Drawing Sheets

U.S. PATENT DOCUMENTS

| | | |
|---|---|---|
| 3,994,423 A | 11/1976 | Burg |
| 3,996,006 A | 12/1976 | Pagano |
| 4,038,570 A | 7/1977 | Durley, III |
| 4,046,513 A | 9/1977 | Johnson |
| 4,084,165 A | 4/1978 | Skafvensted et al. |
| 4,087,332 A | 5/1978 | Hansen |
| 4,193,009 A | 3/1980 | Durley, III |
| 4,216,245 A | 8/1980 | Johnson |
| 4,223,558 A | 9/1980 | Schmider et al. |
| 4,234,103 A | 11/1980 | Strobl, Jr. et al. |
| 4,241,406 A | 12/1980 | Kennedy et al. |
| 4,278,983 A | 7/1981 | Halasz |
| 4,293,867 A | 10/1981 | Isayama |
| 4,308,546 A | 12/1981 | Halasz |
| 4,341,310 A | 7/1982 | Sangiovanni et al. |
| 4,366,490 A | 12/1982 | DeBonte et al. |
| 4,410,020 A | 10/1983 | Lorenz ................... 141/65 |
| 4,418,356 A | 11/1983 | Reece |
| 4,426,031 A | 1/1984 | Halasz |
| 4,447,375 A | 5/1984 | Schimmelpfennig |
| 4,492,322 A | 1/1985 | Hieftje et al. |
| 4,498,088 A | 2/1985 | Kanayama |
| 4,503,012 A | 3/1985 | Starr |
| 4,504,845 A | 3/1985 | Kattner et al. |
| 4,512,722 A | 4/1985 | Mouton |
| 4,514,743 A | 4/1985 | Roschlein et al. |
| 4,518,974 A | 5/1985 | Isayama |
| 4,530,463 A | 7/1985 | Hiniker et al. |
| 4,539,575 A | 9/1985 | Nilsson |
| 4,548,825 A | 10/1985 | Voss et al. |
| 4,550,325 A | 10/1985 | Viola |
| 4,600,928 A | 7/1986 | Braun et al. |
| 4,633,413 A | 12/1986 | Bailey et al. |
| 4,646,104 A | 2/1987 | Braun |
| 4,651,161 A | 3/1987 | Rich et al. |
| 4,672,398 A | 6/1987 | Kuwabara et al. |
| 4,681,741 A | 7/1987 | Hanaway |
| 4,682,710 A | 7/1987 | Turner, Jr. et al. |
| 4,694,850 A | 9/1987 | Kirschmann et al. ........ 222/642 |
| 4,695,852 A | 9/1987 | Scardovi |
| 4,701,754 A | 10/1987 | Provonchee |
| 4,777,832 A | 10/1988 | Prodosmo et al. |
| 4,877,745 A | 10/1989 | Hayes et al. |
| 4,934,419 A | 6/1990 | Lamont et al. ............... 141/94 |
| 4,976,259 A | 12/1990 | Higson et al. |
| 5,039,614 A | 8/1991 | Dekmezian et al. |
| 5,055,263 A | 10/1991 | Meltzer |
| 5,059,393 A | 10/1991 | Quenin et al. |
| 5,072,235 A | 12/1991 | Slowik et al. |
| 5,141,871 A | 8/1992 | Kureshy et al. |
| 5,186,827 A | 2/1993 | Liberti et al. |
| 5,225,750 A | 7/1993 | Higuchi et al. |
| 5,229,679 A | 7/1993 | Higuchi et al. |
| 5,232,664 A | 8/1993 | Krawzak et al. |
| 5,252,294 A | 10/1993 | Kroy et al. |
| 5,297,734 A | 3/1994 | Toda |
| 5,306,510 A | 4/1994 | Meltzer |
| 5,334,353 A | 8/1994 | Blattner |
| 5,356,034 A | 10/1994 | Schlumberger |
| 5,367,783 A | 11/1994 | Zweifel |
| 5,415,679 A | 5/1995 | Wallace |
| 5,449,345 A | 9/1995 | Taylor et al. |
| 5,453,091 A | 9/1995 | Taylor et al. |
| 5,457,527 A | 10/1995 | Manns et al. |
| 5,466,574 A | 11/1995 | Liberti et al. |
| 5,485,828 A | 1/1996 | Hauser |
| 5,525,515 A | 6/1996 | Blattner ................... 436/49 |
| 5,529,754 A | 6/1996 | Bonacina et al. |
| 5,620,004 A | 4/1997 | Johansen |
| 5,630,793 A | 5/1997 | Rowe |
| 5,651,648 A | 7/1997 | Furey |
| 5,653,726 A | 8/1997 | Kieturakis |
| 5,655,446 A | 8/1997 | Watanabe |
| 5,658,723 A | 8/1997 | Oberhardt et al. |
| 5,658,802 A | 8/1997 | Hayes et al. |
| 5,659,173 A | 8/1997 | Putterman et al. |
| 5,661,245 A | 8/1997 | Svoboda et al. |
| 5,663,754 A | 9/1997 | Lorenze et al. |
| 5,673,073 A | 9/1997 | Childers et al. |
| 5,674,238 A | 10/1997 | Sample et al. |
| 5,675,367 A | 10/1997 | Scheffelin et al. |
| 5,681,757 A | 10/1997 | Hayes |
| 5,682,236 A | 10/1997 | Trolinger |
| 5,685,310 A | 11/1997 | Porter |
| 5,685,848 A | 11/1997 | Robinson et al. |
| 5,690,907 A | 11/1997 | Lanza et al. |
| 5,691,478 A | 11/1997 | Barry et al. |
| 5,693,016 A | 12/1997 | Gumaste et al. |
| 5,694,919 A | 12/1997 | Rubsamen et al. |
| 5,694,946 A | 12/1997 | Tenerz et al. |
| 5,695,457 A | 12/1997 | St. Goar et al. |
| 5,695,461 A | 12/1997 | Schaible |
| 5,695,468 A | 12/1997 | Lafontaine et al. |
| 5,695,740 A | 12/1997 | Porter |
| 5,697,375 A | 12/1997 | Hickey |
| 5,698,018 A | 12/1997 | Bishop et al. |
| 5,700,848 A | 12/1997 | Soon-Shiong et al. |
| 5,701,899 A | 12/1997 | Porter |
| 5,702,384 A | 12/1997 | Umeyama et al. |
| 5,705,062 A | 1/1998 | Knobel et al. |
| 5,763,278 A | 6/1998 | Sickinger et al. |
| 5,843,767 A | 12/1998 | Beattie |
| 5,950,681 A * | 9/1999 | Reimelt |

FOREIGN PATENT DOCUMENTS

| | | |
|---|---|---|
| DE | 4 140 533 | 6/1993 |
| DE | 0 301 771 | 11/1993 |
| DE | 19 532382 | 3/1997 |
| EP | 0 012 821 | 11/1979 |
| EP | 0 024 230 | 2/1981 |
| EP | 0 270 558 | 2/1983 |
| EP | 0 119 573 | 9/1984 |
| EP | 0 169 071 | 1/1986 |
| EP | 0 202 022 | 11/1986 |
| EP | 0 219 177 | 4/1987 |
| EP | 0 268 237 | 5/1988 |
| EP | 0 412 431 | 2/1991 |
| EP | 0 432 992 | 6/1991 |
| EP | 0 438 136 | 7/1991 |
| EP | 0 446 972 | 9/1991 |
| EP | 0 465 749 | 1/1992 |
| EP | 0 508 531 | 10/1992 |
| EP | 0 513 441 | 11/1992 |
| EP | 0 545 284 | 6/1993 |
| EP | 0 548 872 | 6/1993 |
| EP | 0 568 024 | 11/1993 |
| EP | 0 581 708 | 2/1994 |
| EP | 0 628 413 | 12/1994 |
| EP | 0 655 256 | 5/1995 |
| EP | 0 712 232 | 5/1996 |
| EP | 0 718 046 | 6/1996 |
| EP | 0 747 689 | 12/1996 |
| EP | 0 761 256 | 3/1997 |
| EP | 0 763 742 | 3/1997 |
| EP | 0 766 946 | 5/1997 |
| EP | 0 779 436 | 6/1997 |
| EP | 0 781 987 | 7/1997 |
| EP | 0 788 809 | 8/1997 |
| EP | 0 789 383 | 8/1997 |
| EP | 0 795 409 | 9/1997 |
| EP | 0 810 096 | 12/1997 |

| | | |
|---|---|---|
| EP | 0 810 438 | 12/1997 |
| ES | 2073992 | 8/1995 |
| JP | 55-79167 | 12/1978 |
| JP | 1-038147 | 2/1989 |
| JP | 1-150549 | 6/1989 |
| JP | 01234144 | 9/1989 |
| JP | 2-017079 | 1/1990 |
| RU | 0 783 635 | 11/1980 |
| RU | 0 791 954 | 12/1980 |
| RU | 0 858 845 | 9/1981 |
| RU | 1 089 420 | 4/1985 |
| RU | 1 262 376 | 10/1986 |
| RU | 1 436 057 | 11/1988 |
| RU | 1 740 007 | 6/1992 |
| RU | 2011961 | 4/1994 |
| RU | 400042 | 8/1997 |
| WO | WO 92/15256 | 9/1972 |
| WO | WO 89/00725 | 1/1989 |
| WO | WO 89/10193 | 11/1989 |
| WO | WO 90/11040 | 10/1990 |
| WO | WO 92/11050 | 7/1992 |
| WO | WO 92/15361 | 9/1992 |
| WO | WO 92/18608 | 10/1992 |
| WO | WO 93/10910 | 6/1993 |
| WO | WO 94/06568 | 3/1994 |
| WO | WO 95/01559 | 1/1995 |
| WO | WO 95/04502 | 2/1995 |
| WO | WO 95/26236 | 10/1995 |
| WO | WO 95/35212 | 12/1995 |
| WO | WO 96/12609 | 5/1996 |
| WO | WO 97/16251 | 5/1997 |
| WO | WO 99/28494 | 6/1999 |
| WO | WO 99/36576 | 7/1999 |
| WO | WO 99/53102 | 10/1999 |
| WO | WO 99/61881 | * 12/1999 |
| WO | WO 00/09738 | 2/2000 |

OTHER PUBLICATIONS

Beach et al., "Materials Selection for an Ink Jet Printer" pp. 75–86, IBM J. Res. Develop.

Boillat et al., "A Differentail Pressure Liquid Flow Sensor for Flow Regulation and Dosing Systems," Proceedings IEEE, Micro Electro Mechanical Systems, MEMS, '95 Amsterdam.

Buehner, et al., "Application of Ink Jet Technology to a Word Processing Output Printer", pp. 1–9, IBM J. Res. Develop.

Carmichael, "Controlling Print Height in an Ink Jet Printer" 52–55, IBM J. Res. Develop.

Curry, Portig, "Scale Model of an Ink Jet" pp. 10–20, IBM J. Res. Develop.

Filmore et al. Drop Charging and Deflection in an Electrostatic Ink Jet Printer, pp. 37–47, IBM J. Res. Develop.

Holcombe, Eklund & Grice, "Vaporization and Atomization of Large Particles in an Acetylene/Air Flame", pp. 2097–2103, Analytical Chemistry, vol. 50, No. 14, Dec. 1978.

Joshi and Sacks "Circular Slot Burner–Droplet Generator System for High–Temperature Reaction and Vapor Transport Studies", pp. 1781–1785, Analytical Chemistry, vol. 51, No. 11, Sep. 1979.

Lee "Boundary layer Around a Liquid Jet" pp. 48–51, IBM J. Res. Develop.

Levanoni, "Study of Fluid Flow through Scaled–up Ink Jet Nozzles" pp. 56–68, IBM J. Res. Develop.

Microdrop Instruction Manual, Microdrop Gesellschaft für Mikrodosiersysteme mbH, MD–K–130SP/140H/135/150 and Drive electronics MD–E–204, May 1994.

Microdrop Instruction Manual, Microdrop Gesellschaft für Mikrodosiersysteme MbH, AD–E–130, Sep. 1995.

Microdrop Literature, "Flussigkeiten mikrofein dosieren" Gesellschaft for Mikrodosiersysteme mbH, 1994 (in the German language).

Microdrop literature, "Microdosing in the picoliter range with piezo technology" sales brochure from Microdrop Gesellschaft Für Mickrodosiersysteme mbH, Oct., 1995.

Pimbley "Satellite Droplet Formation in a Liquid Jet" pp. 21–30, Satellite Formation, IBM J. Res. Develop.

Plunkett, Matthew J. et al., "Combinatorial Chemistry and New Drugs", Scientific American, Apr. 1997, P. 69–73.

Schober, A., et al., "Accurate High–Speed Liquid Handling of Very Small Biological Samples," BioTechniques, vol. 15, No. 2 (1993), p, 324–329.

Twardeck "Effect of Parameter Variations on Drop Placement in an Electrostatic Ink Jet Printer" pp. 31–36, IBM J. Res. Develop.

Zengerle et al., "Carbon Dioxide Priming of Micro Liquid Systems", *IEEE* (1995), pp. 340–343.

J. M. Köhler et al., "Micromechanical elements for detection of molecules and molecular design", pp. 202–208, Microsystem Technologies, Springer–Verlag 1995.

European Search Report Application Number EP 00 97 3512, dated Sep. 30, 2002.

* cited by examiner

PIEZOELECTRIC-DROP-ON-DEMAND TECHNOLOGY

RELATED APPLICATIONS

This application is a complete application of provisional U.S. application Ser. No. 60/159,701, filed Oct. 15, 1999 and a continuation-in-part of U.S. application Ser. No. 09/489,261, filed Jan. 21, 2000 which is a continuation-in-part of U.S. application Ser. No. 09/056,233, filed Apr. 7, 1998, which is a conventional application of provisional U.S. application Ser. No. 60/041,861, filed Apr. 8, 1997, and provisional U.S. Application No. 60/067,665, filed Dec. 5, 1997, and a continuation-in-part of U.S. application Ser. No. 08/656,455, filed May 31, 1996, now abandoned.

BACKGROUND OF THE INVENTION

This invention relates to aspirating and dispensing small volumes of liquids. In particular, it relates to automatic aspirating and dispensing of small volumes of liquids, typically for analytical purposes.

It is possible to accurately aspirate and dispense submicroliter volumes of liquid for analytical applications and to accurately verify the volume of liquid dispensed. The liquid may contain chemically or biologically active substances.

It is also possible to monitor in real time the dispensing of single 100 micron or smaller drops of liquid.

One of the primary factors for successful operation of micromachined or capillary-based piezoelectric-drop-on-demand technology is the ability to keep the dispensers clean.

Multiple technologies exist to clean the outside of the tips by flushing or jetting liquid at the orifice of the dispenser. Dispenser tips can also be immersed in ultrasonic baths to dislodge particles and molecules from the surface of the dispensers.

While these technologies are very effective at cleaning the outside of the dispenser, they do not thoroughly remove deposits adhering to the interior walls. A piezoelectric-drop-on-demand capillary has a very small bore orifice of approximately 5 to 100 $\mu$m and, therefore, cannot be scrubbed by standard mechanical means like a brush or cloth.

Magnetic particles have been associated with various types of separation processes. In recent years magnetic particles have been used to adhere to biological materials to facilitate separation of such materials from the medium in which they are located. One example is found in U.S. Pat. No. 5,895,631 where a high molecular substance is bonded to magnetic particles, which are then attracted to the wall of a container by an external magnetic force. The particles could be removed by releasing the magnetic force which attached the particles to the wall and then flushing them from the container. Similarly, magnetic particles find a new use in the present invention which provides a means for cleaning the interior of the capillary tips used for dispensing 100 micron or smaller drops of liquid.

SUMMARY OF THE INVENTION

In accordance with one aspirating and dispensing apparatus, 1 to 100 micron range drops of liquid are accurately deposited onto various types of locations, typically for analytical purposes.

In another aspect, subnanoliter drops of liquid are dispensed and a pressure change resulting from the droplet ejection is detected. A known volume of a compressible fluid, e.g., a gas such as air, facilitates measuring small changes in system pressure which correlate to the volume of the transfer liquid which has been dispensed.

In accordance with still another aspect, subnanoliter drops of liquid are dispensed, and a pressure change resulting from ejection of a drop of a transfer liquid is detected by an electrical signal which indicates that single drops of liquid are dispensed at millisecond intervals. By eliminating all compressible fluids (gases) from the liquid in the system, the ejection of picoliter size drops can be detected. The dispensed drops are generally in the range of from about 5 to about 500 picoliters, often about 100 to about 500 picoliters.

Subnanoliter droplets of liquid are ejected and the volume of the drops can be measured in real time. Electrical signals indicating transient pressure changes in the transfer liquid upon dispensing liquid drops (in the range of from about 5 to about 500 picoliters, preferably about 100 to about 500 picoliters) can be detected when the liquid in the enclosed volume of the dispenser is connected to a liquid reservoir. As long as substantially all compressible fluids (gases) are kept out of the dispensing conduit (which communicates through a restricted passage to the liquid reservoir), the pressure sensor of the system of the present invention can detect dispensing a single drop of liquid in the range of from about 5 to about 500 picoliters, preferably about 100 to about 500 picoliters. The pressure change resulting from ejection of such a drop occurs in a time period long enough for the pressure change to be detectable, but short enough to complete the cycle before the next drop is ejected.

The invention particularly relates to a means for cleaning the interior of the capillary tubes used to dispense such small droplets, the cleaning being carried out by magnetic particles aspirated into the capillary tubes and moved by a magnet outside the capillary tubes to dislodge deposits adhering to the inner walls.

Other aspects of the present invention will become apparent to those skilled in the art upon studying this disclosure.

DESCRIPTION OF ILLUSTRATIVE EMBODIMENTS

The present invention in particular relates to a feature useful in the aspirating and dispensing apparatus described in parent application Ser. No. 09/056,233 and below.

Description of a First Aspirating and Dispensing Apparatus

The system constructed in accordance with the first aspirating and dispensing apparatus of the present invention includes a system liquid and a transfer liquid separated by a known volume of compressible fluid, e.g., a gas such as air ("air gap"). The air gap facilitates measuring small changes in pressure in the system liquid. The change in pressure is proportional to the volume of transfer liquid dispensed. One preferred system liquid is deionized water. As a result of capillary forces, each time a droplet in the microvolume dispensing range is dispensed, the transfer liquid will return to its prior position inside the microdispenser. The specific volume of the air gap will be increased proportionally to the amount of transfer liquid dispensed. The result is a decrease in pressure in the system liquid line which is measured with a highly sensitive piezoresistive pressure sensor. The pressure sensor transmits an electric signal which controls circuitry. The electric signal is converted into a digital form which is indicative of the volume of transfer liquid dispensed. An advantage of the present invention is its insensitivity to the viscosity of the transfer liquid. The pressure change in the system liquid corresponds to the microvolume dispensed, without being dependent on the viscosity of the dispensed liquid.

The first aspirating and dispensing apparatus of the present invention provides a microvolume liquid handling system which includes a positive displacement pump operated by a stepper motor, a piezoresistive pressure sensor, and an electrically controlled microdispenser that utilizes a piezoelectric transducer bonded to a glass capillary. The microdispenser is capable of rapidly and accurately dispensing sub-nanoliter ("nl") sized droplets by forcibly ejecting the droplets from a small nozzle, this process is known as "drop-on-demand." Specifically, the dispenser of the present invention dispenses drops in the range of from about 5 to about 500 picoliters, preferably from about 100 to about 500 picoliters.

To provide the functionality of an automated liquid handling system, the microdispensers in all preferred embodiments are mounted onto a 3-axis robotic system that is used to position the microdispensers at specific locations required to execute the desired liquid transfer protocol.

Figure 1:
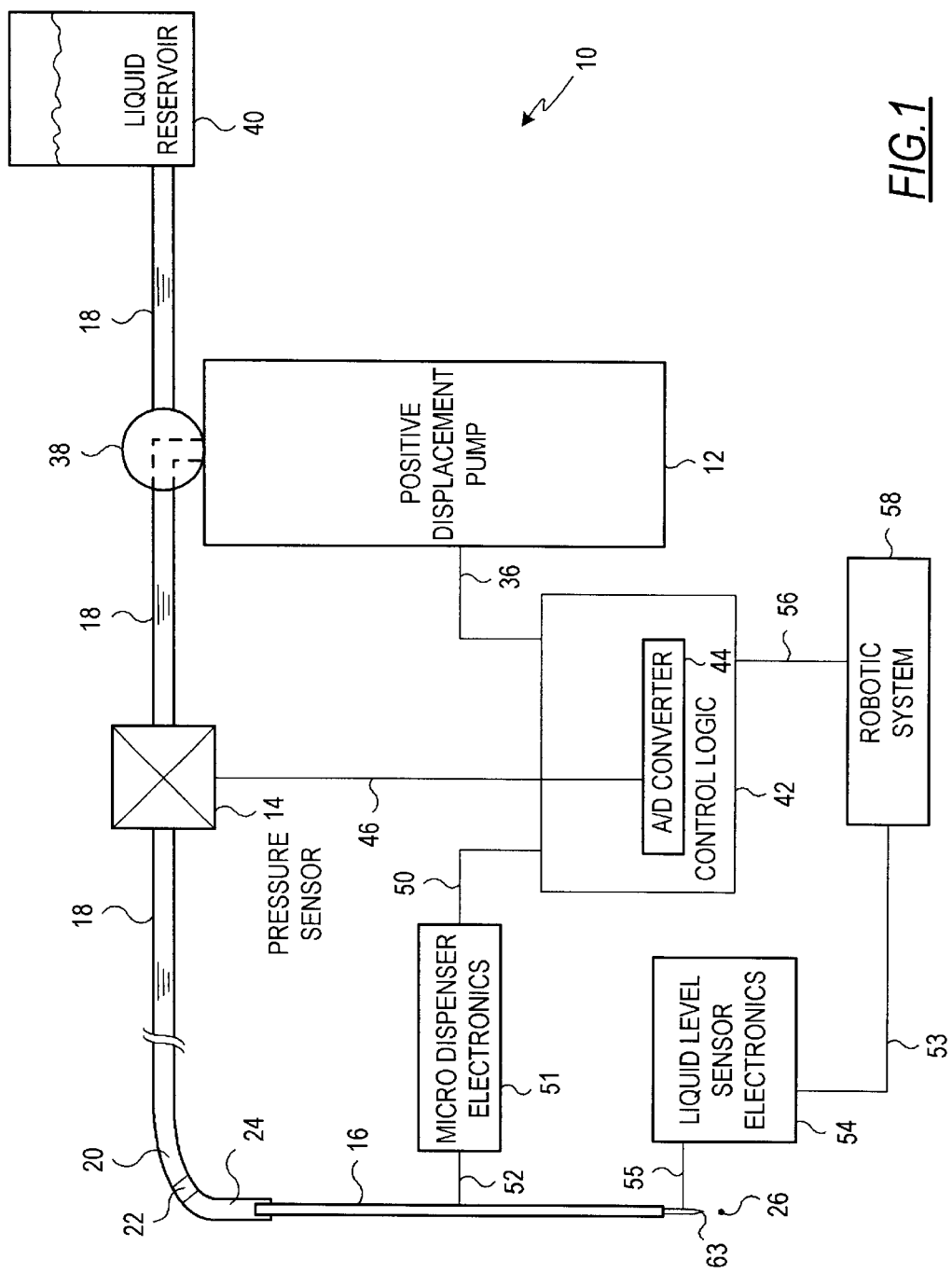
FIG. 1 is a block diagram of a system for aspirating and dispensing microvolumes of liquid illustrating the first aspirating and dispensing apparatus.

Referring first to FIG. 1, a first microvolume liquid handling system 10 is illustrated, and includes a positive displacement pump 12, a pressure sensor 14, and a microdispenser 16. Tubing 18 connects the positive displacement pump 12 to the pressure sensor 14 and the pressure sensor 14 to the microdispenser 16. The positive displacement pump 12 moves a system liquid 20 through the pressure sensor 14 and the microdispenser 16. After the system 10 is loaded with system liquid 20, an air gap 22 of known volume is provided. An amount of transfer liquid 24 is drawn into the microdispenser 16 in a manner described below. The transfer liquid 24 can contain one or more biologically or chemically active substances of interest. Preferably, the microdispenser 16 expels (or, synonymously, "shoots") sub-nanoliter size individual droplets 26 which are very reproducible. The expelled droplets 26 of transfer liquid 24 are generally in the range of about 5 to about 500 picoliters, preferably about 100 to about 500 picoliters per droplet 26. For example, if one desires to expel a total of 9 nanoliters of transfer liquid 24, the microdispenser 16 will be directed to expel 20 droplets 26, each having a volume of 0.45 nanoliters. Droplet 26 size can be altered by varying the magnitude and duration of the electrical signal applied to the microdispenser 16. Other factors affecting droplet size include: size of the nozzle opening at the bottom of the microdispenser, pressure at the microdispenser inlet, and certain properties of the transfer liquid.

Figure 2:
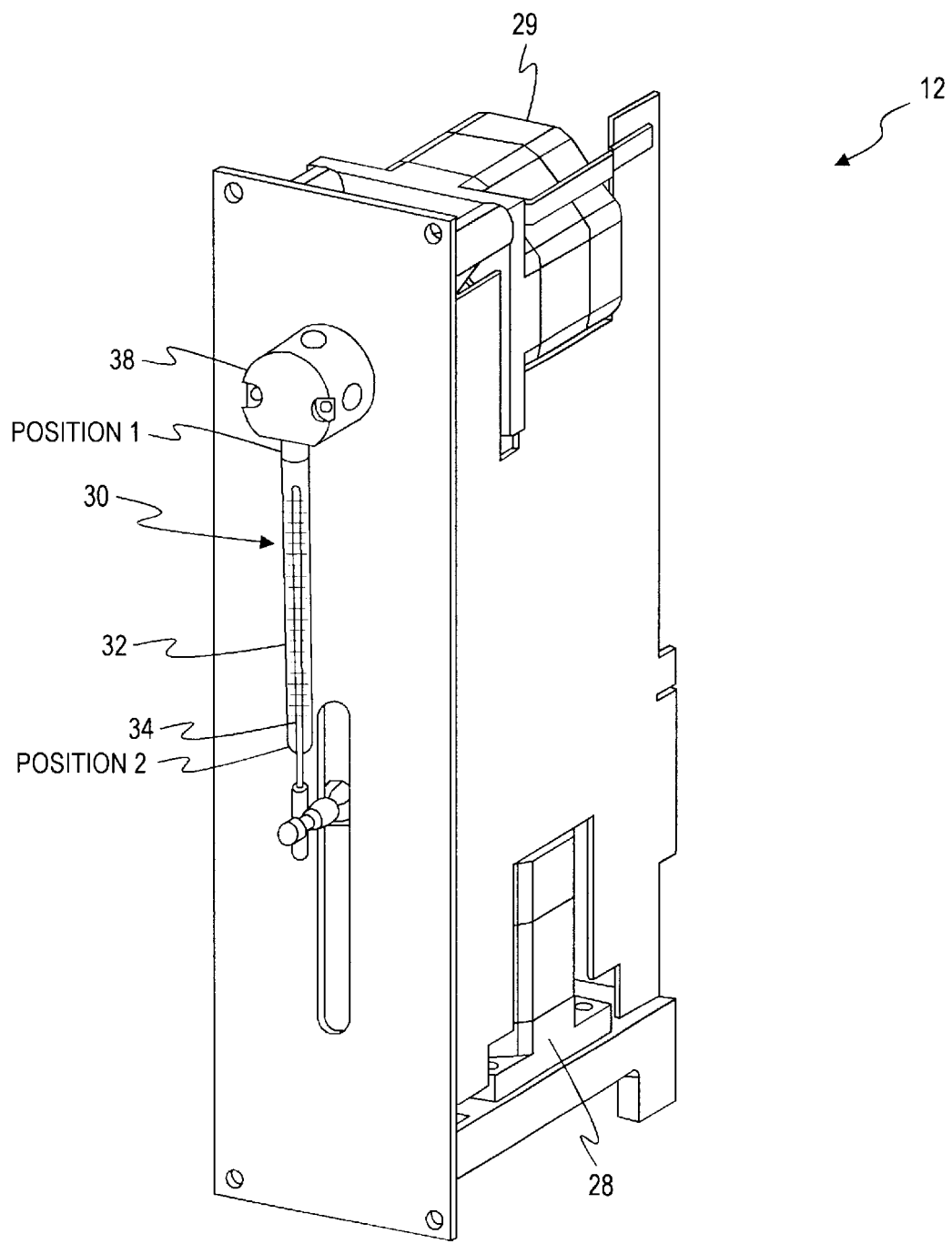
FIG. 2 is a schematic of a positive displacement pump used in the system of FIG. 1.

Referring now to FIGS. 1 and 2, in one preferred embodiment, the positive displacement pump 12 is an XL 3000 Modular Digital Pump, manufactured by Cavro Scientific Instruments, Inc., Sunnyvale, Calif. The positive displacement pump 12 includes stepper motor 28, stepper motor 29, and a syringe 30. The syringe 30 includes a borosilicate glass tube 32 and a plunger 34 which is mechanically coupled through a series of gears and a belt (not shown) to the stepper motor 28. Stepper motor 28 motion causes the plunger 34 to move up or down by a specified number of discrete steps inside the glass tube 32. The plunger 34 forms a liquid-tight seal with the glass tube 32. In one preferred embodiment, syringe 30 has a usable capacity of 250 microliters, which is the amount of system liquid 20 the plunger 34 can displace in one full stroke. Depending on the selected mode of operation, the stepper motor 28 is capable of making 3,000 or 12,000 discrete steps per plunger full 34 stroke. In one preferred embodiment, the stepper motor 28 is directed to make 12,000 steps per plunger 34 full stroke, with each step displacing approximately 20.83 nanoliters of system liquid 20. In one preferred embodiment, the system liquid 20 utilized is deionized water.

Digitally encoded commands cause the stepper motor 28 within the positive displacement pump 12 to aspirate discrete volumes of liquid into the microdispenser 16, wash the microdispenser 16 between liquid transfers, and control the pressure in the system liquid 20 line for microvolume liquid handling system 10 operation. The positive displacement pump 12 is also used to prime the system 10 with system liquid 20 and to dispense higher volumes of liquid through the microdispenser 16, allowing the dilution of certain system liquids. The positive displacement pump 12 can also work directly with transfer liquid 24. Thus, if desired, transfer liquid 24 can be used as system liquid 20 throughout the microvolume liquid handling system 10.

To prime the microvolume liquid handling system 10, the control logic 42 first directs a 3-axis robotic system 58 through electrical wire 56 to position the microdispenser 16 over a wash station contained on the robotic system 58. In one preferred embodiment, the microvolume liquid handling system 10 includes, and is mounted on, a 3-axis robotic system, the MultiPROBE CR10100, manufactured by Packard Instrument Company. The positive displacement pump 12 includes a valve 38 for connecting a system liquid reservoir 40 to the syringe 30. An initialization control signal is transmitted through the electrical cable 36 to the pump 12 by control logic 42. This causes the valve 38 to rotate (by means of stepper motor 29), connecting the syringe 30 with the system liquid reservoir 40. The control signal also causes the stepper motor 28 to move the plunger 34 to its uppermost position (Position 1 in FIG. 2) in the borosilicate glass tube 32. The next command from the control logic 42 causes the stepper motor 28 to move the plunger 34 to its lowermost position (Position 2 in FIG. 2) in the tube 32 and to extract system liquid 20 from the system reservoir 40. Another command from the control logic 42 directs the valve 38 to rotate again, causing the syringe 30 to be connected with the tubing 18 that is, in turn, connected to the pressure sensor 14. In one preferred embodiment, the tubing 18 employed in the microvolume liquid handling system 10 is Natural Color Teflon Tubing, manufactured by Zeus Industrial Products, Inc., Raritan, N.J., with an inner diameter of 0.059 inches and an outer diameter of 0.098 inches. The next command from the control logic 42 to the positive displacement pump 12 causes the system liquid 20 inside the syringe 30 to be pushed into the microvolume liquid handling system 10 towards the pressure sensor 14. Because the microvolume liquid handling system 10 typically requires about 4 milliliters of system liquid to be primed, the sequence of steps described above must be repeated about 16 times in order to completely prime the microvolume liquid handling system 10.

The control logic 42 receives signals from the pressure sensor 14 through an electrical line 46. The signals are converted from an analog form into a digital form by an A/D (analog to digital) converter 44 and used by the control logic 42 for processing and analysis. In one preferred embodiment, the A/D converter is a PC-LPM-16 Multifunction I/O Board, manufactured by National Instruments Corporation, Austin, Tex. At various points in the liquid transfer process described herein, the control logic 42 receives signals from the pressure transducer 14, and sends command signals to the pump 12, microdispenser electronics 51, and the 3-axis robotic system 58. Within the control logic 42 exist the encoded algorithms that sequence the hardware (robotic system 58, pump 12, and microdispenser electronics 51) for specified liquid transfer protocols, as described herein. Also within the control logic 42 are the encoded algorithms that process the measured pressure signals to verify and quantify microdispenser, perform diagnostics on the state of the microvolume liquid handling system, and automatically perform a calibration of the microdispenser for any selected transfer liquid 24.

The pressure sensor 14 detects fluctuations in pressure that occur with priming the microvolume liquid handling system 10, aspirating transfer liquid 24 with a pump 12, dispensing droplets 26 with the microdispenser 16, and washing of the microdispenser 16 with a pump 12. In one preferred embodiment, the pressure sensor 14 is a piezoresistive pressure sensor, part number 26PCDFG6G, manufactured by Microswitch, Inc., a division of Honeywell, Inc., Freeport, Ill. Also included with the pressure sensor 14 in the block diagram in FIG. 1 is electrical circuitry which amplifies the analog pressure signal from the pressure sensor. The pressure sensor 14 converts pressure into electrical signals which are driven to the A/D converter 44 and used by the control logic 42. For example, when the microvolume liquid handling system 10 is being primed, the pressure sensor 14 sends electrical signals which are analyzed by the control logic 42 to determine whether they indicate partial or complete blockage in the microdispenser 16.

Once the microvolume liquid handling system 10 is primed, the control logic 42 sends a signal through electrical wire 56 which instructs the robotic system 58 to position the microdispenser 16 in air over the transfer liquid 24. The control logic 42 instructs the stepper motor 28 to move the plunger 34 down, aspirating a discrete quantity of air (air gap), e.g., 50 microliters in volume, into the microdispenser 16. The control logic 42 then instructs the robotic system 58 to move the microdispenser 16 down until it makes contact with the surface of the transfer liquid 24 (not shown). Contact of the microdispenser 16 with the surface of the transfer liquid 24 is determined by a capacitive liquid level sensing system (U.S Pat. No. 5,365,783). The microdispenser is connected by electrical wire 55 to the liquid level sense electronics 54. When the liquid level sense electronics 54 detects microdispenser 16 contact with the transfer liquid 24 surface, a signal is sent to the robotic system 58 through electrical wire 53 to stop the downward motion.

The control logic 42 instructs the pump 12 to move the plunger 34 down to aspirate the transfer liquid 24 into the microdispenser 16. To ensure that the transfer liquid is successfully drawn into the microdispenser, the pressure signal is monitored by control logic. If a problem, such as an abnormal drop in pressure due to partial or total blockage of the microdispenser is detected, the control logic 42 will send a stop movement command to the pump 12. The control logic 42 will then proceed with an encoded recovery algorithm. Note that the transfer liquid 24 can be drawn into the microvolume liquid handling system 10 up to the pressure sensor 14 without the threat of contaminating the pressure sensor 14. Additional tubing can be added to increase transfer liquid 24 capacity. Once the transfer liquid 24 has been aspirated into the microdispenser 16, the control logic 42 instructs the robotic system 58 to reposition the microdispenser 16 above the chosen target, e.g., a microtiter plate or a wafer.

In one preferred embodiment, the microdispenser 16 is the MD-K-130 Microdispenser Head, manufactured by Microdrop, GmbH, Norderstedt, Germany.

Figure 3:
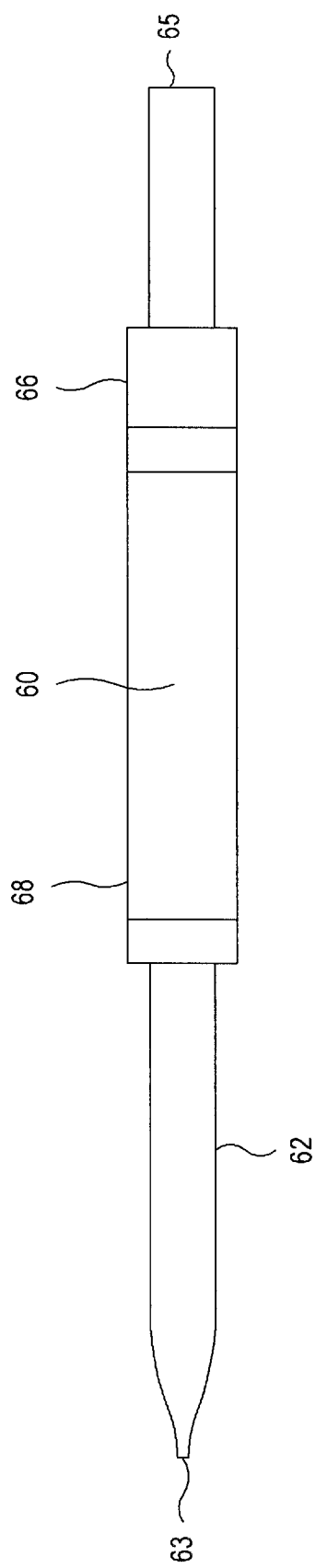
FIG. 3 is side plan view of a microdispenser including a piezoelectric transducer.

As illustrated in FIG. 3, the microdispenser 16 consists of a piezoceramic tube 60 bonded to a glass capillary 62. The piezoceramic tube has an inner electrode 66 and an outer electrode 68 for receiving analog voltage pulses which cause the piezoceramic tube to constrict. Once the glass capillary 62 has been filled with transfer liquid 24, the control logic 42 directs the microdispenser electronics 51 to send analog voltage pulses to the piezoelectric transducer 60 by electrical wire 52. In one preferred embodiment, the microdispenser electronics 51 is the MD-E-201 Drive Electronics, manufactured by Microdrop, GmbH. The microdispenser electronics 51 control the magnitude and duration of the analog voltage pulses, as well as the frequency at which the pulses are sent to the microdispenser 16. Each voltage pulse causes a constriction of the piezoelectric transducer 60 which, in turn, deforms the glass capillary 62. The deformation of the glass capillary 62 produces a pressure wave that propagates through the transfer liquid 24 to the microdispenser nozzle 63, where one highly accelerated droplet 26 of transfer liquid 24 is emitted. The size of these droplets 26 has been shown to be very reproducible. The high acceleration of the transfer liquid 24 minimizes or eliminates problems caused by transfer liquid 24 surface tension and viscosity, thus allowing extremely small (e.g., 5 picoliter) droplets 26 to be expelled from the nozzle. Use of the microdispenser 16 to propel droplets 26 out of the nozzle circumvents problems encountered in the liquid transfer technique referred to "touchoff." In the touchoff technique, a droplet 26 is held at the end of a nozzle and is deposited onto a target surface by bringing that droplet 26 into contact with the target surface while it is still suspended from the microdispenser 16. Such a contact process is susceptible to unacceptable volume deviations as a result of surface tension, viscosity and wetting properties of the microdispenser 16 and the target surface. The present invention avoids the problems of the contact process because the droplets 26 are expelled out of the microdispenser 16 at a velocity of several meters per second. The total desired volume is dispensed by the present invention by specifying the number of droplets 26 to be expelled. Because thousands of droplets 26 can be emitted per second from the microdispenser 16, the desired microvolume of transfer liquid 24 can rapidly be dispensed.

In one preferred embodiment, the lower section of the glass capillary 62, located between the piezoelectric transducer 60 and the nozzle 63, is plated with a conductive material, typically platinum or gold. The use of this material provides an electrically conductive path between the microdispenser 16 and the liquid level sense electronics 54. In one preferred embodiment, the glass capillary 62 has an overall length of 73 millimeters and the nozzle 63 has an internal diameter of 75 micrometers.

To dispense microvolume quantities of transfer liquid 24, analog voltage pulses are sent to the microdispenser 16, thus emitting droplets 26 of liquid. Capillary forces acting on the transfer liquid 24 replace the volume of transfer liquid 24 emitted from the microdispenser 16 with liquid from the tubing 18. Since the transfer liquid-air gap system liquid column terminates at a closed end in the positive displacement pump 12, however, there is a corresponding drop in the system liquid 20 line pressure as the air gap 22 is expanded. This may be seen in FIG. 4 of parent application Ser. No. 09/056,233. The magnitude of the pressure drop is a function of the size of the air gap 22 and the volume of the liquid dispensed.

With an air gap 22 of known volume, the pressure change as detected by the pressure sensor 14 is proportional to the volume dispensed. Thus, from the pressure change measured by the pressure sensor 14, the control logic determines the volume of transfer liquid 24 that was dispensed. In one preferred embodiment of the present invention, depending on the properties of the transfer liquid, it is preferable that the drop in pressure not exceed approximately 30 to 40 millibars below ambient pressure. If the amount of transfer liquid 24 dispensed is sufficient to drop the pressure more than 30 to 40 millibars, the pressure difference across the microdispenser 16 (i.e., the difference between the ambient pressure acting on the nozzle 63 and the pressure at the capillary inlet 65) will be sufficient to force the transfer liquid 24 up into the tubing 18. This will preclude further dispensing. There is a maximum amount of transfer liquid 24 that can be dispensed before the control logic 42 is required to command the pump 12 to advance the plunger 34 to compensate for the pressure drop. This maximum volume is determined by the desired dispense volume and the size of the air gap 22. Conversely, the size of the air gap 22 can be selected based on the desired dispense volume so as not to produce a pressure drop exceeding 30 to 40 millibars below ambient pressure. It is also within the scope of the present invention to advance the plunger 34 while the microdispenser 16 is dispensing, thereby rebuilding system liquid 20 line pressure so that the microdispenser 16 can operate continuously.

The change in system liquid 20 pressure is used to verify that the desired amount of transfer liquid 24 was dispensed. A second verification of the amount of transfer liquid 24 that was dispensed is made by the control logic 42 that monitors the system liquid 20 line pressure while directing the pump 12 to advance the syringe plunger 34 upwards towards Position 1. The syringe plunger 34 is advanced until the system liquid 20 line pressure returns to the initial (pre-dispense) value. Because the control logic 42 tracks the displaced volume, the plunger 34 moves (20.83 nanoliters per stepper motor 28 step) and a second confirmation of the volume dispensed is made, thus adding robustness to the system. After a second dispensing verification, the system liquid 20 line pressure is now at the correct value for the next dispensing action if a multi-dispense sequence has been specified.

Once the transfer liquid 24 dispensing has been completed, the control logic 42 causes the robotic system 58 to position the microdispenser 16 over the wash station. The control logic 42 then directs pump 12 and robotic system 58 in a wash protocol that disposes of any transfer liquid 24 left in the microdispenser 16. This protocol also results in washes to the internal surface of the glass capillary 62 and the external surface in the nozzle 63 area that was exposed to transfer liquid 24. The wash liquid can either be system liquid 20 or any other liquid placed onto the deck of the robotic system 58. The wash protocol is designed to minimize cross-contamination of different transfer liquids 24 used during different dispensing sessions. Towards this end, it is also possible to use a high frequency pulsing of the transducer 60 to facilitate washing of the microdispenser 16. This is accomplished using the control logic 42 to direct the microdispenser electronics 51 to send electrical pulses to the microdispenser at a frequency in the range of from about 1 to about 20 Khz (the preferred resonant frequency of the microdispenser 16 is believed to be approximately 12 kilohertz). The resonant frequency of the microdispenser coincides with the resonant frequency of the microdispenser 16—transfer liquid 24 system. Pulsing the piezoelectric transducer 60 at the above frequencies causes the interior surfaces of the glass capillary 62 to vibrate vigorously. System liquid 20, or a special cleaning and/or neutralizing liquid, is used to flush out the microdispenser 16 while the piezoelectric transducer 60 is activated at the above-described frequencies. Cleaning with high frequency pulsing is more efficient at dislodging and eliminating matter adhering to the microdispenser 16. For example, it has been shown in a number of test cases that such cleaning caused a 200 to 500% improvement (depending on the contaminant) in the reduction of residual matter in the microdispenser 16 compared to cleaning without such pulsing.

Pulsing of the microdispenser 16 is also used to prevent, minimize or alleviate clogging of the nozzle of the microdispenser. For example, when transfer liquid is being aspirated into the microdispenser 16, it must pass through the relatively narrow nozzle 63 in the glass capillary 62. Matter in the transfer liquid 24 often comes into contact with the nozzle's 63 surfaces, permitting the matter to adhere to the nozzle 63. In biochemical applications, one widely used matter added to the transfer liquid 24 is polystyrene spheres. These spheres typically range from 1 micron to over 30 microns, and may be uncoated or coated with magnetic ferrites, antigens or other materials. The relatively large size of the polystyrene spheres with regard to nozzle 63 diameter, in combination with their sometimes glutinous coatings, can cause the spheres to adhere to the nozzle 63. It has been found that if the piezoelectric transducer 60 is excited at high frequency while the microdispenser 16 is being loaded (i.e., transfer liquid 24 is being aspirated into the microdispenser 16), clogging may be prevented or minimized. Thus, high frequency pulsing of the microdispenser 16 prevents or diminishes clogging of the nozzle 63 by materials in the transfer liquid 24.

Anytime a transfer liquid 24 containing dissolved or suspended materials passes through the nozzle 63, the possibility of clogging occurs. Not only is clogging a problem during aspiration of transfer liquid 24 into the microdispenser 16 as described above, but it is also a problem when transfer liquid is dispensed from the high frequency pulsing of the microdispenser 16. Droplet dispensing by the piezoelectric transducer can reduce buildup of materials adhering to the nozzle 63 and, thus, prevent clogging in some instances. Even if substantial clogging does occur, high frequency pulsing of the microdispenser 16 by the piezoelectric transducer 60 will substantially clear the clogging materials from the nozzle 63. The key advantage to this cleaning strategy is continuous instrument operation without the delays associated with alternate cleaning procedures. In short, system downtime is reduced, making the microvolume liquid handling system 10 more efficient.

In certain applications, such as those described above, the liquid being dispensed adheres to the inner walls of the capillary tip and, despite the pulsing with the piezoelectric transducer, additional cleaning is required. It has been found that abrasive magnetic particles can be used to clean the capillary tips by manipulating them with an external magnet.

In the above description of the invention, the control of the microdispenser 16 occurs via electrical pulses from the microdispenser electronics 51, with each pulse resulting in an emitted droplet 26 of transfer liquid 24. It is also within the scope of the invention to control the microdispenser 16 by monitoring the pressure sensor 14 signal in real time, and continuing to send electrical pulses to the microdispenser 16 until a desired change in pressure is reached. In this mode of operation, the PC-LPM-16 Multifunction I/O Board that contains the A/D converter 44 is instructed by control logic 42 to send electrical pulses to the microdispenser electronics 51. Each pulse sent by the Multifunction I/O Board results in one electrical pulse sent by the microdispenser electronics 51 to the microdispenser 16, emitting one droplet 26 of transfer liquid 24. The control logic 42 monitors the pressure sensor 14 signal as dispensing is in progress. Once the desired change in pressure has been attained, the control logic 42 directs the Multifunction I/O Board to discontinue sending electrical pulses.

This mode of operation is employed if a "misfiring" of microdispenser 16 has been detected by control logic 42.

It is also within the scope of the invention for the microvolume liquid handling system 10 to automatically determine the size of the emitted droplets 26 for transfer liquids 24 of varying properties. As heretofore mentioned, emitted droplet 26 size is affected by the properties of the transfer liquid 24. Therefore, it is desirable to be able to automatically determine emitted droplet 26 size so that the user need only specify the total transfer volume to satisfy the user requirements. In the encoded autocalibration algorithm, once the system 10 is primed, an air gap 22 and transfer liquid 24 are aspirated, and the control logic 42 instructs the microdispenser electronics 51 to send a specific number of electrical pulses, e.g., 1000, to the microdispenser 16. The resulting drop in pressure sensor 14 signal is used by the control logic 42 to determine the volume of transfer liquid 24 that was dispensed. The control logic verifies the volume of liquid dispersed by tracking the volume displaced by the movement of the plunger 34. The system subsequently restores the liquid line pressure to the pre-dispense value.

The microvolume liquid handling system 10 illustrated in FIG. 1 depicts a single microdispenser 16, pressure sensor 14, and pump 12. It is within the spirit and scope of this invention to include embodiments of microvolume liquid handling systems that have a multiplicity (e.g., 4, 8, 96) of microdispensers 16, pressure sensors 14, and pumps 12. It is also within the spirit and scope of this invention to include embodiments of microvolume liquid handling systems that have a multiplicity of microdispensers 16, pressure sensors 14, valves 38, and one or more pumps 12.

Description of a Second Aspirating and Dispensing Apparatus

Figure 4:
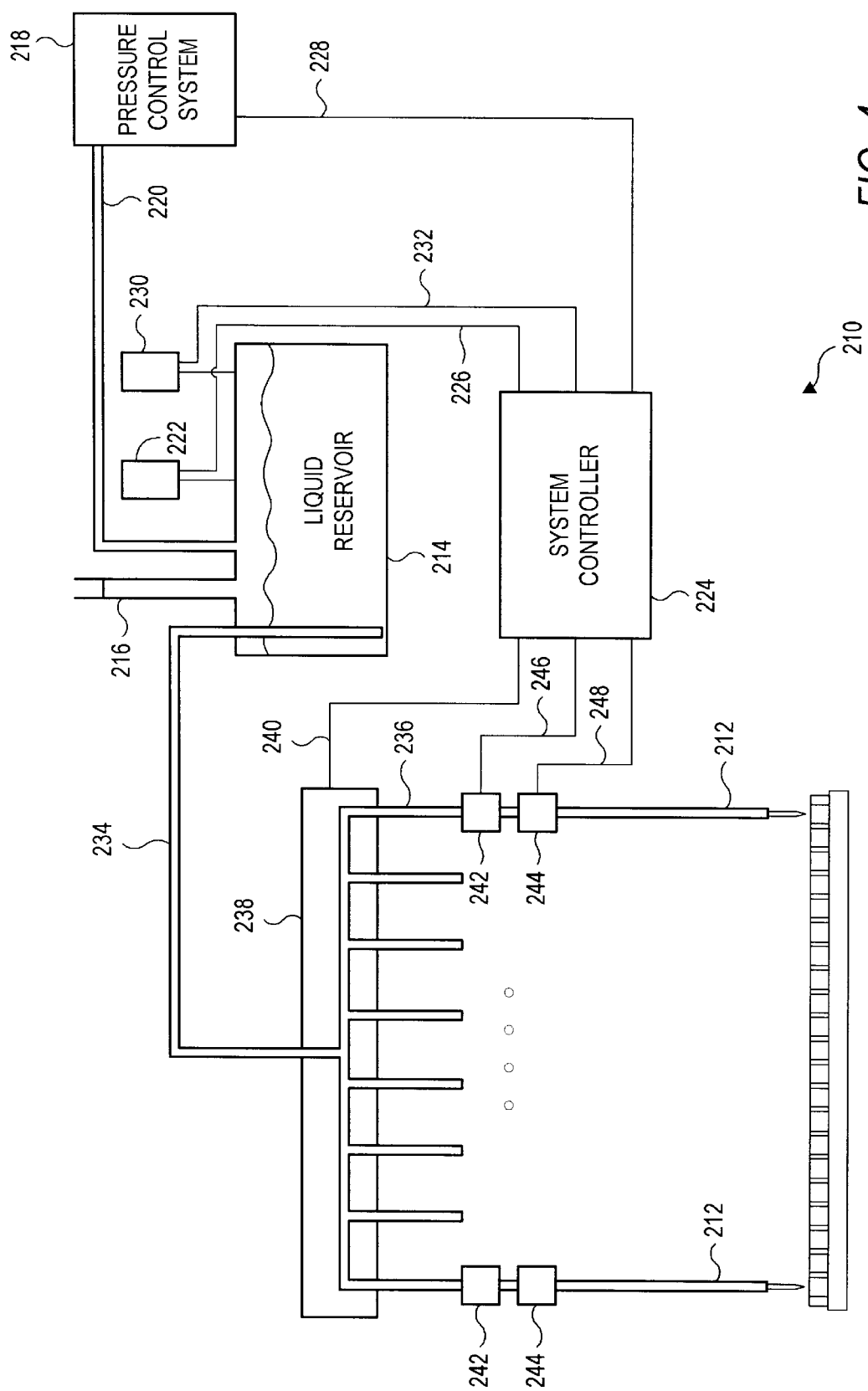
FIG. 4 is a block diagram of a system for aspirating and dispensing microvolumes of liquid illustrating the second aspirating and dispensing apparatus.

In FIG. 4, another aspirating and dispensing apparatus 210 is shown. This embodiment, which is preferred when the number of microdispensers employed is equal to or greater than eight, also realizes the aforementioned objectives. The second apparatus is similar to the first shown in FIG. 1, except that the positive displacement pump (which includes a valve as described below), the stepper motor, and the piezoresistive pressure sensor are replaced with a pressure control system for supplying and controlling system liquid pressure. This embodiment also employs a plurality of flow sensors for detecting liquid flow, as well as pressure in the system liquid which is present in the connecting tubing that is coupled to each microdispenser. It also employs a plurality of valves (such as solenoid or microfabricated valves), each valve coupling each microdispenser to a system reservoir in the pressure control system. In this apparatus, a system liquid reservoir 214 is used to supply system liquid 20 to all the microdispensers 212, thus eliminating the separate pump and pressure sensor for each microdispenser 212 utilized in the first apparatus. Note that first and second embodiments are otherwise identical in structure and operation except as described herein. The precise number of microdispensers employed is a function of the user's dispensing requirements.

With regard to the second embodiment, the system liquid reservoir 214 receives system liquid 20, typically deionized water or dimethyl sulfoxide (DMSO), through an intake tube 216 which contains a cap (not separately shown). The cap on the intake tube 216 is removed to enable the sealed system liquid reservoir 214 to receive system liquid 20 when the cap is off, and seals the system liquid reservoir 214 shut when the cap is on so that the system liquid reservoir 214 can be maintained at a desired pressure. Pressure in the system liquid reservoir 214 is maintained by a pressure control system 218 through the use of pressure control tubing 220. The pressure control system 218 includes an electrically controlled pump capable of accurately increasing or decreasing pressure in the system liquid reservoir 214. A pressure sensor 222 mounted on the system liquid reservoir 214 senses pressure in the system liquid reservoir 214 and transmits an electrical signal indicative of that pressure to a system controller 224 through an electrical conductor 226. The system controller 224 contains a digital signal processor board and other electronics (not shown) which enable monitoring of various electrical signals, execution of control software code, and control of the microvolume liquid handling system 210. The system adjusts the pressure of the system liquid 20 and, correspondingly, the pressure of the transfer liquid 24 via an electrical conductor. A pressure relief valve 230 is mounted on the system liquid reservoir 214. The pressure relief valve 230 releases pressure from the system liquid reservoir 214 when the pressure exceeds a predetermined safety threshold. In one embodiment, the pressure relief valve 230 can also be opened by the system controller 224 which is connected to the pressure relief valve 230 by a wire 232.

During operations, the system controller 224 directs the pressure control system 218 to maintain one of three different pressure levels in the system reservoir 214 with regard to ambient atmospheric pressure. Each of the three pressure levels corresponds to a different phase of operation of the microvolume liquid handling system 210. The three different pressure levels include a positive pressure, a high negative pressure, and a low negative pressure. Prior to dispensing, positive pressure is used to clean the microdispenser. High frequency pulsing of the microdispensers 212 is also employed in the manner described above. After the microdispensers 212 are relatively clean, the high negative pressure levels (roughly 200 millibars less than the ambient atmospheric pressure) is used to aspirate transfer liquid 24 into the microdispensers 212. Once the transfer liquid 24 has been aspirated into the microdispensers 212, the low negative pressure levels (roughly −15 millibars gauge) are used to supply back pressure to the transfer liquid 24 in the microdispensers 212 such that as droplets are dispensed, no additional transfer liquid 24 leaves the microdispensers 212.

System liquid 20 in the system reservoir 214 is coupled to the microdispensers 212 through a distribution tube 234 that splits into a plurality of sections 236, as shown in FIG. 4, with one section 236 connected to each microdispenser 212.

Attached to each of the distribution tube sections 236 are solenoid valves 242 and flow sensors 244. The system controller 224 sends electrical signals through an electrical connection 246 to control the valves 242. A flow sensor 244 is attached to each distribution tube section 236 to determine the amount of liquid that is being aspirated into each microdispenser. The flow sensor 244 detects the flow of system liquid 20 into or out of each microdispenser 212. The flow sensors 244 are each connected to the system controller 224 through an electrical conductor 248. The electrical conductor 248 carries electrical signals from each flow sensor 244, indicating not only the amount of liquid flow, but also the pressure in each flow sensor. The flow sensors 244 are microfabricated. This is advantageous since the sensors are small and fit easily into the microvolume liquid handling system 210. An example of the flow sensors 244 is described in IEEE Proceedings, MEMS 1995, Publication No. 0-7803-2503-6, entitled, "A Differential Pressure Liquid Flow, Sensor For Flow Regulation and Dosing Systems," by M. Boillat et al., hereby incorporated by reference.

The distribution tube 234, which is physically connected to the microdispensers 212, is attached to a three axis robot 238. As in the first preferred embodiment, the microdispensers are relocated to positions above different microtiter plates, wells or wafers. After the desired number of droplets has been dispensed, the robot 238 moves the microdispensers 212 to the next set of wells or wafers for further dispensing. The dispensing heads can be stationary and the robotic system can be used to locate the source and destination vessels.

It has been discovered that the ejection of individual drops of a transfer liquid in the volume range of about 100 to about 500 picoliters can be detected using the system of the present invention with a pressure detector. In order to detect dispensing of such drops, the transfer and system liquids must be substantially free of compressible gases, such as air. As used herein, the term "substantially free of compressible gas" means that the level of compressible gas, if any, is low enough to allow the detection of a drop of liquid being ejected from the system. It has been discovered that as the amount of compressible gas in the system increases, the ability to detect dispensing of the drop decreases until, at a certain level of compressible gas, the system cannot detect dispensing of a drop of the transfer liquid.

In accordance with one embodiment of the present invention, the volume from the dispensing nozzle, which holds the transfer liquid to the valve (242 in FIG. 4), is substantially free of compressible gas and is entirely enclosed. It has been discovered that in this preferred embodiment of the present invention, drops can be ejected from the closed volume until the pressure in the fluid is reduced to about –45 millibars gauge. At about –45 millibars gauge the vacuum interferes with the ejection of the drops.

In accordance with another embodiment of the present invention, the volume from the dispensing nozzle to the reservoir of system liquid is substantially free of compressible fluid (gas). It has been discovered that upon dispensing a drop of liquid, the system of this embodiment can detect a pressure change in the system liquid resulting from such drop being dispensed. The pressure change is transient. As the transfer liquid flows into the volume adjacent to the nozzle, effectively replacing the ejected drop volume, the pressure rises to the level prior to the dispensing of the drop. It has been discovered that for dispensing drops in the size range of from about 100 to about 500 picoliters, the time required for the pressure to reach the original level can be in a range of from about 5 to about 10 milliseconds. This time period can be controlled by selecting the size and confirmation of the orifice located between the volume that is adjacent to the nozzle and the reservoir. It has been determined that purging the air out of the system with a fluid (gas) that has a high solubility coefficient with respect to the system liquid has greatly reduced the residual compressible fluid (gas) in the system after priming with system liquid. Once the system is primed, keeping compressible fluids (e.g., air) out of the system is facilitated by degassing the system liquid, pressurizing the system liquid reservoir with an inert gas, utilizing low permeability tubing, and also degassing system liquid in-line. To aid in elimination of air bubbles, carbon dioxide purging can be employed as described in IEEE Proceedings, MEMS 1995, Publication No. 0-7803-2503-6, entitled "Carbon Dioxide Priming Of Micro Liquid Systems," by R. Zengerle et al.

An example of the ability of the system to dispense single drops is provided in parent application Ser. No. 09/056,233, and illustrated in FIGS. 8–11.

In accordance with another aspect of the present invention, several methods have been developed to minimize the amount of transfer liquid that needs to be aspirated into the dispenser. In the system of the present invention, which is capable of monitoring the ejection of single drops, the dispensing chamber has to be free of compressible fluids (gas) in order for the drops to be ejected. This requires that the chamber from the nozzle (63 in FIG. 3) to the top of the piezoelectric transducer (60 in FIG. 3) be filled with liquid. This volume is often large in comparison to the volume of transfer liquid to be dispensed.

In accordance with one method, the system liquid and the transfer liquid are not separated from each other by an air gap, as shown in FIG. 1. Instead, the two liquids are separated by a liquid which is immiscible with either or both the transfer liquid and the system liquid.

In accordance with another method, to minimize the required aspirate volume of transfer liquid, system liquid is used to fill the dispenser before aspiration of the transfer liquid begins. It has been discovered that, as the transfer liquid is aspirated, the system liquid mixes with the transfer liquid at the interface slowly enough to allow dispensing of a large percentage of the transfer liquid without observing a dilution of the transfer liquid with the system liquid.

In embodiments which do not require use of a separate system liquid, a single liquid can be used to serve as both the system liquid and the transfer liquid.

In accordance with a further aspect of the present invention, the pressure in the dispenser (such as in dispenser 212 of FIG. 4) decreases as a result of a reduction in the system liquid reservoir (214 in FIG. 4) pressure. The valve (242 in FIG. 4) is closed, and then the nozzle of the dispensing unit can be immersed in the transfer liquid to aspirate a small quantity of the transfer liquid into the dispenser. For example, when gauge pressure in the dispenser reaches –30 millibars, submersing the nozzle in the transfer liquid may draw a sufficient amount of liquid to increase the gauge pressure to –15 millibars. It should be noted that the dispenser does not aspirate air unless the surface tension in the nozzle is exceeded by the negative gauge pressure. In the system of the preferred embodiment using dimethyl sulfoxide, the negative gauge pressure of 45 millibars does not produce air aspiration into the nozzle.

The systems described can automatically detect when the microdispenser orifice enters into a liquid and when it is withdrawn.

A pressure-based liquid detection function has been developed for the embodiments shown in FIGS. 1 and 4.

This function can be used to detect when one or more micro dispensers is immersed in or withdrawn from liquid. This determination is made based on a pressure change which occurs when the microdispensers are immersed in or withdrawn from liquid. This pressure change is measured by monitoring the pressure transducer (14 in FIG. 1) or flow sensors (244 in FIG. 4). This test is performed independently for each system microdispenser.

The liquid determination process can be divided into three distinct stages.

1. Predelay

Upon receipt of a "liquid level sense" command, the algorithm allows for a user-specified predelay to be performed. The duration of the delay allows the completion of an external event (i.e., the movement of the head to an aspiration source) to occur before the software begins to look for the pressure change of an air/liquid transition. Certain external events may result in a false positive if these events trigger a pressure change. This function allows the system to identify any spurious pressure change.

In the event that the predelay is zero, the software will begin monitoring the pressure immediately upon receipt of the "liquid level sense" command. This can also be applied in systems where the microdispensers are stationary and the robotic system moves the source, or aspiration vessel.

2. Baseline Establishment

Once the predelay has expired, a baseline pressure value is established from the average of multiple readings. This baseline pressure value will then be compared to subsequent pressure readings to determine if they differ enough to indicate an air-liquid transition.

3. Liquid Detect

The last stage is utilized to compare the established baseline pressure value with the current pressure values. The current pressure value is a rolling average. This ensures that a single spurious point will not result in an incorrect liquid detection event. During this stage, the pressure is read periodically. The oldest pressure value is then removed, the newest pressure value added, and a new average calculated. This average is then compared with the baseline which was established in the previous stage. The difference between these values is assessed via a user-specified threshold value. If the magnitude of the difference is greater than the threshold, then the algorithm will conclude that a liquid detect event has occurred and will set the liquid detected states to the control logic. The same test is performed independently for each dispenser.

The algorithm will continue to monitor the system for liquid detection events until a user-specified detection duration has expired. If no pressure transition of the specified magnitude occurs during this duration, the software will notify the control logic that no air-liquid transition has occurred for that particular dispenser.

The user-specified threshold value, in units of millibar, is used to refine the liquid detection process. If true air-liquid transitions are occurring, but are not being identified, then the threshold value can be decreased, thus enhancing detection sensitivity. If false liquid-detection determinations are being made as a result of random pressure fluctuations, the threshold value can be increased, thus diminishing detection sensitivity. The pressure threshold has a positive or negative value associated with it, thus enabling the user to activate the liquid detection function when the microdispensers are either immersed in or withdrawn from liquid.

Cleaning With Magnetic Particles

Figure 5:
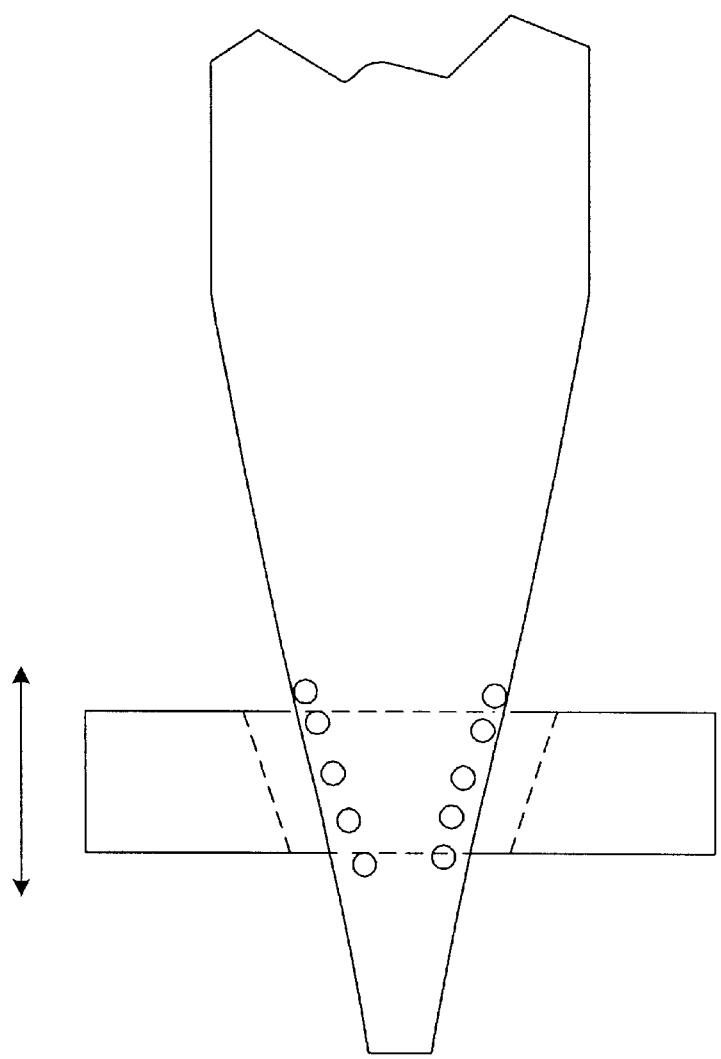
FIG. 5 illustrates the use of a magnet in combination with magnetic particles to remove deposits adhering to the inner walls of a capillary tip.

As previously discussed, capillary tubes may be pulsed at high frequency to prevent or eliminate clogging. When more complete cleaning is required, abrasive magnetic particles may be aspirated into the tip and moved by an external magnet to remove deposits on the inner wall of the capillary. The concept is illustrated in FIG. 5. Magnetic particles, for example those used to bind and extract DNA, RNA, and the like from solutions, may be used to clean the interior walls of capillary tubes as described above. Although such particles are convenient, since they are commercially available and are capable of binding the deposits, other types of fine magnetic particles may be used. The particles must be small enough to pass through the capillary tip easily and are typically about 0.2 to 4 $\mu$m in diameter. Also, they must have sufficient interaction with magnets outside the capillary to be moved against the interior wall of the capillary with sufficient force to dislodge adhering deposits.

FIG. 5 illustrates schematically the interaction of a ring magnet surrounding a capillary tip. Either the magnetic is moved to move the particles or alternatively, the capillary tip may be moved as was done in the following example. The piezoelectric transducer may be used to assist removing the deposits and magnetic particles while flushing the capillary tube.

EXAMPLE

Nucleotide quality magnetic particles obtained from Promega were added to a solution of CY3-labeled oligonucleotide material having a concentration of 0.1 $\mu$g/$\mu$L in a 50 m molar borate buffer.

A piezoelectrically-operated capillary tip was flushed for 4 seconds over a standard washbowl, then 10 $\mu$L of the magnetic particle containing solution was aspirated into the capillary tube. After which, the capillary tube was moved up and down in another washbowl containing a ring magnet having an internal diameter of 2 mm and external diameter of 7 mm, while a wash fluid was flushed through the capillary tube to remove dislodged deposits. Finally, the capillary tube was moved to the original washbowl and the remaining fluid containing the magnetic particles binding the oligonucleotide material was expelled from the capillary tip.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the scope of the claimed invention, which is set forth in the following claims.

What is claimed is:

1. A method of removing deposits adhering to the interior walls of a capillary tube having inner and outer walls:
    (a) aspirating into said capillary tube a liquid containing magnetic particles having a size smaller than said capillary tube inner wall;
    (b) positioning a magnet outside said capillary tube for attaching said magnetic particles of (a) to positions adjacent said inner wall;
    (c) moving said magnet relative to said capillary or said capillary relative to said magnet, thereby causing said magnetic particles to move adjacent to said inner wall and loosen said deposits; and
    (d) discharging said liquid containing said magnetic particles and said deposits loosened from said inner wall.

2. A method of claim 1, wherein said magnetic particles have a nominal diameter of about 0.2 to 4 $\mu$m.

3. A method of claim 1, wherein said capillary tube has a piezoelectric transducer mounted on the exterior of said tip.

4. A method of claim 3, wherein said discharging of step (d) is carried out while activating said piezoelectric transducer.

5. A method of claim 1, wherein said aspirating of step (a) is carried out by applying a negative pressure within said capillary tube.

6. A method of claim 1, wherein said discharging of step (d) is carried out by applying a positive pressure within said capillary tube.

7. A method of claim 1, wherein said magnetic particles are coated with a material capable of binding said deposits.

8. A method of claim 7, wherein said magnetic particles bind said deposits loosened from said inner wall.

9. A method of claim 1, further comprising flushing said capillary tube with a wash fluid during step (c).

* * * * *